United States Patent
Jäger et al.

(10) Patent No.: US 11,908,574 B2
(45) Date of Patent: Feb. 20, 2024

(54) REMOTE CONTROL FOR A MEDICAL APPARATUS, SYSTEM OF THE REMOTE CONTROL AND THE MEDICAL APPARATUS AND METHOD FOR OPERATING THE MEDICAL APPARATUS

(71) Applicant: TRUMPF MEDIZIN SYSTEME GMBH + CO. KG, Saalfeld (DE)

(72) Inventors: Matthias Jäger, Rudolstadt (DE); Matthias Köhler, Saalfeld (DE); Leonard Zeh, Saalfeld (DE); Nick Neuendorf, Konigsee (DE); Bertram Müller, Neuhaus am Rennweg (DE)

(73) Assignee: TRUMPF MEDIZIN SYSTEME GMBH + CO. KG, Saalfeld (DE)

( * ) Notice: Subject to any disclaimer, the term of this patent is extended or adjusted under 35 U.S.C. 154(b) by 523 days.

(21) Appl. No.: 17/072,113

(22) Filed: Oct. 16, 2020

(65) Prior Publication Data

US 2021/0035683 A1    Feb. 4, 2021

Related U.S. Application Data (63) Continuation-in-part of application No. 16/935,820, filed on Jul. 22, 2020.

(30) Foreign Application Priority Data

Jul. 29, 2019  (EP) ................................. 19188807
Oct. 17, 2019  (EP) ................................. 19203771

(51) Int. Cl.
*G16H 40/63*    (2018.01)

(52) U.S. Cl.
CPC .................. *G16H 40/63* (2018.01)

(58) Field of Classification Search
CPC ........ G16H 40/67; G16H 40/63; G16H 20/40; A61G 13/02; A61G 2203/12
USPC ........................................ 700/83; 340/12.54
See application file for complete search history.

(56) References Cited

U.S. PATENT DOCUMENTS

| | | | |
|---|---|---|---|
| 5,517,300 A | * | 5/1996 | Parker .................... B25J 9/1697 348/169 |
| 2009/0126115 A1 | | 5/2009 | Doering et al. |
| 2012/0118718 A1 | | 5/2012 | Geiger et al. |
| 2013/0147611 A1 | * | 6/2013 | Brendel ................. G08C 17/02 340/12.5 |
| 2015/0245965 A1 | | 9/2015 | Griesel et al. |
| 2017/0049524 A1 | * | 2/2017 | Olson ................. G06F 3/03545 |

(Continued)

FOREIGN PATENT DOCUMENTS

| | | |
|---|---|---|
| DE | 19751329 A1 | 5/1999 |
| EP | 2455959 A1 | 5/2012 |

*Primary Examiner* — Md Azad
(74) *Attorney, Agent, or Firm* — Barnes & Thornburg LLP (57) ABSTRACT

A remote control for controlling a medical apparatus having at least one driven movable components is provided. The remote control comprises a sensor configured to detect a position and a motion of the remote control, and at least one release switch. The remote control is configured to emit a control signal capable of controlling a motion of the at least one driven movable component according to a motion of the remote control detected by the sensor when a control of the motion of the at least one driven movable component is released by actuating the at least one release switch.

20 Claims, 5 Drawing Sheets

(56) References Cited

U.S. PATENT DOCUMENTS

2017/0154158 A1\* 6/2017 Marka .................... A61B 6/548
2017/0196748 A1 7/2017 Gaiser \* cited by examiner

REMOTE CONTROL FOR A MEDICAL APPARATUS, SYSTEM OF THE REMOTE CONTROL AND THE MEDICAL APPARATUS AND METHOD FOR OPERATING THE MEDICAL APPARATUS

CROSS-REFERENCE TO RELATED APPLICATIONS

This application claims the benefit of European Patent Application Serial No. 19203771.1, filed on Oct. 17, 2019. This application is a continuation-in-part of U.S. patent application Ser. No. 16/935,820, filed Jul. 22, 2020 which claims benefit of European Patent Application Serial No. 19188807.2, filed on Jul. 29, 2019. The entire disclosure of each of these applications is incorporated herein by reference in their entirety.

TECHNICAL FIELD

The present disclosure relates to a remote control for a medical apparatus, a system of the remote control and the medical apparatus, and a method for operating the medical apparatus. In particular, the present disclosure is directed to a remote control for a medical apparatus having several movable segments driven in a controlled manner, a system of the remote control and the medical apparatus, and a method for operating the medical apparatus.

BACKGROUND

A remote control for a medical apparatus which controls motions of movable segments of the medical apparatus is generally adapted for security against unintended use. To achieve this, the remote control usually includes at least one release switch and several switches for controlling motions in different directions of the respective movable segments. EP2455959A1 discloses such a remote control. However, in particular, in case of an operating table as the medical apparatus, the number of movable components, i.e., the movable segments or other movable components of the operating table is extensive. Therefore, the number of the switches actuated by buttons or soft keys of a touch screen increased and the existing remote controls had, due to the increased number of buttons or soft keys, challenges in that the operation of the operating table becomes cumbersome and uncomfortable. Furthermore, an intuitive operation, in particular, an adjustment of a speed of the motion of the movable components is not provided. The present disclosure addresses these limitations to overcome the above disadvantages and to provide a remote control for a medical apparatus enabling a comfortable operation of the medical apparatus in an intuitive manner.

SUMMARY

The present disclosure includes one or more of the features recited in the appended claims and/or the following features which, alone or in any combination, may comprise patentable subject matter.

According to a first aspect of the present disclosure, a remote control for controlling a medical apparatus having at least one driven movable component comprises a sensor configured to detect a position and a motion of the remote control, and at least one release switch. The remote control is configured to emit a control signal capable of controlling a motion of the at least one driven movable component according to a motion of the remote control detected by the sensor when a control of the motion of the at least one driven movable component is released by actuating the at least one release switch. By such a remote control, merely pressing of one button or one soft key for actuating the release switch may be necessary for emitting a specific control signal since, after the release by the release switch, the control signal may then emitted due to the motion of the remote control itself.

In an embodiment of the remote control, the remote control may be configured to emit the control signal according to a direction of the motion of the remote control detected by the sensor with respect to a position of the remote control when the at least one release switch is actuated to start the release of the control of the motion of the at least one driven movable component. When the control signal is emitted according to the direction of the motion of the remote control, an intuitive operation or motion of the movable component may be simply possible by moving the remote control according to a desired motion of the movable component.

In a further embodiment of the remote control, the remote control may be configured to emit the control signal according to an amount of the motion of the remote control. By emitting the control signal according to the amount of the motion of the remote control, a more precise command including characteristics of the motion of the remote control can be emitted for controlling the medical apparatus easily in an intuitive manner.

In a yet further embodiment of the remote control, the remote control may be configured to emit the control signal according to a speed of the motion of the remote control. By emitting the control signal according to the speed of the motion of the remote control, also, a more precise command including characteristics of the motion may be emitted for comfortably controlling the medical apparatus in an intuitive manner.

According to another embodiment of the remote control, the remote control may comprise a display configured to detect a location of a contact of an object. Such a touch display or touchscreen may enable an easy change of soft keys provided for different medical apparatuses or different configurations of one kind of medical apparatuses. Moreover, different languages or pictograms for denoting the soft keys may be presented for an easy operation of the remote control.

In a still further embodiment of the remote control, the remote control may a display configured to display a preview of the motion of the at least one driven movable component according to the control signal. By this display, an operator may easily verify the intended motion of the medical apparatus.

According to yet another embodiment of the remote control, the remote control may have an elongated shape and a first axis parallel to the elongated shape of the remote control and a second axis perpendicular to the elongated shape of the remote control, and the remote control may be configured to emit the control signal according to a direction of the motion of the remote control around at least one of the first axis and the second axis. In this embodiment, easy and unambiguous motions of the remote control may be used for determining the motion of the movable component of the medical apparatus so that the intuitive operation of the medical apparatus is easily possible and the remote control may be operated easier.

In a still further embodiment of the remote control, the remote control may be configured to emit the control signal according to the direction of the motion of the remote control around at least one of the first axis and the second axis if the motion of the remote control around the at least one of the first axis and the second axis exceeds a predefined threshold. By the emission of the control signal not before exceeding a predefined threshold of the motion of the remote control around the at least one of the first axis and the second axis, the remote control can be operated more easily since a motion of the remote control is not required in a very exact manner and an unintended operation around one of the first and second axis is quite safe prevented.

According to a second aspect of the present disclosure, a system of the remote control and the medical apparatus is provided. The remote control may be configured to control the motion of the at least one driven movable component of the medical apparatus by the control signal. By the provision of this system, the medical apparatus may be comfortably operated without a need for searching an appropriate button or soft key for operating a specific motion of the movable component of the medical apparatus.

In an embodiment of the system, the remote control may be configured to control a direction of the motion of the at least one driven movable component according to a direction of the motion of the remote control with respect to a position of the remote control when the at least one release switch starts to release the control of the motion. By this characteristic, the motion of the movable component may be initiated intuitively so that the operation of the medical apparatus may be facilitated.

In an embodiment of the system, the remote control may comprise several release switches, the medical apparatus comprises several driven movable components respectively driven by a driving device, and the several release switches are respectively assigned to a specific motion of one of the driven movable components. In such a system, several movable components of the medical apparatus may be controlled in an easy and intuitive manner. On the one hand, if one movable component performs several motions, for example, by one release switch, a height adjustment of a tabletop of an operating table can be released and, by another release switch, tilting of the tabletop around its longitudinal axis may be released, therefore, the several release switches release the control of the motions of one movable component. On the other hand, if merely one motion is executed by one of the driven movable component, the control of this motion may be released, so that the several release switches release the motions of several driven movable components.

In a further embodiment of the system, the medical apparatus may comprise at least one driven movable component which performs several motions respectively driven by a driving device, and the system may be configured such that the several motions are controlled by the remote control when the several motions of the at least one driven movable component are released by a release button assigned to the at least one driven movable component, wherein the several motions may be controlled according to motions of the remote control around a first axis parallel to an elongated shape of the remote control and a second axis perpendicular to the elongated shape of the remote control. In this embodiment, easy and unambiguous motions of the remote control may be used for determining the motion of the movable component of the medical apparatus so that the intuitive operation of the medical apparatus may be easily possible and the remote control may be operated more easily since no further release switches for releasing the several motions of the at least one driven movable component are necessary.

In an embodiment of the system, the medical apparatus may be configured as an operating table. In particular, an operating table can comprise a large quantity of driven movable segments for adjusting the position of a patient in a surgical treatment and of other driven movable components. Moreover, there may be a necessity for adjusting the movable segments during surgery. Therefore, the easy and intuitive operation of the operating table is a tremendous advantage.

In a further embodiment of the system, one of the at least one driven components may be formed by a locking device configured to lock a motion of the operating table by touching a face supporting the operating table. By providing this component and by operating this component by means of the remote control, a position of the operating table before a surgical intervention can be easily secured and after the surgical intervention, the operating table the secured position can be easily released in an intuitive manner.

In a yet further embodiment of the system, one of the at least one driven components may be formed by a wheel of the operating table, wherein the wheel comprises a drive and the wheel may be configured to move the operating table by the drive. By the provision of the driven wheel controlled by the remote control, the motion of the operating table together with the patient into an operating theatre and out of an operating theatre may be easily possible in an easy and intuitive manner of controlling.

According to third aspect of the present disclosure, a method for operating a medical apparatus by means of a remote control comprises the steps: releasing a control of a motion of a specific one of driven movable components of the medical apparatus by actuating a specific release switch of the remote control and controlling a motion of the specific one of the movable components by moving the remote control with respect to a position of the remote control when the specific release switch starts to release the control of the motion of the specific one of the movable components. By the provision of this method, the driven movable components of the medical apparatus may be operated without a need for searching an appropriate button or soft key for operating a specific motion of the movable component of the medical apparatus.

In an embodiment of the method, a direction of the motion of the specific one of the driven movable components may be defined by a direction of motion of the remote control around at least one of an axis parallel to an elongated shape of the remote control and an axis perpendicular to the elongated shape of the remote control. In this embodiment of the method, easy and unambiguous motions of the remote control are used for determining the motion of the movable component of the medical apparatus so that the intuitive operation of the medical apparatus may be easily possible.

In a still further embodiment of the method, the motion of the specific one of the driven movable components may be stopped when the remote control is moved into a horizontal position. By this embodiment, stopping of the motion of the movable components is easily and intuitively possible.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
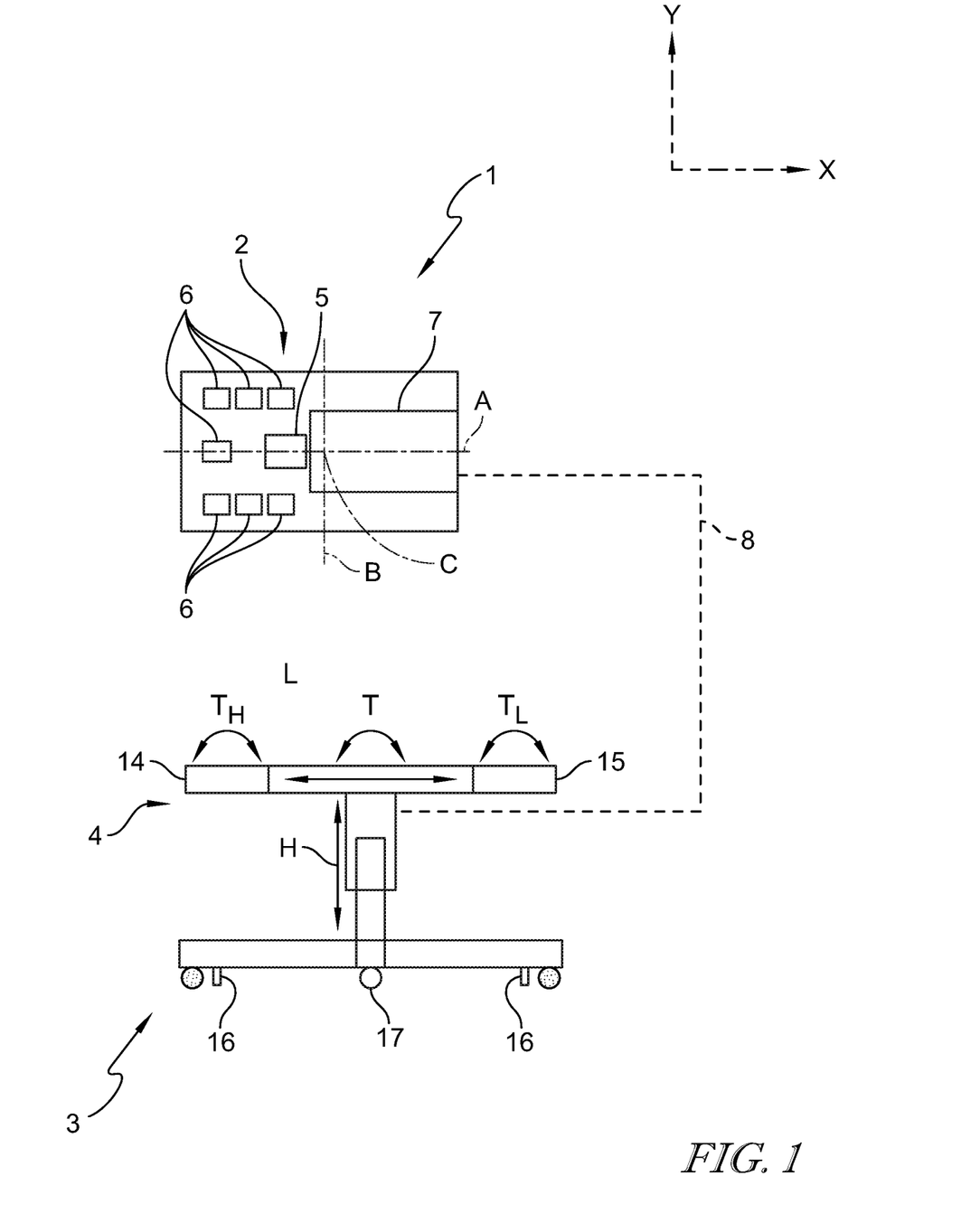
FIG. 1 shows a system of a remote control in a schematic plan view and of an operating table in a schematic side view.

FIG. 1 shows a system 1 according to the present disclosure including a remote control 2 in a schematic plan view and an operating table as an embodiment of a medical apparatus 3 in a schematic side view.

The medical apparatus 3 comprises several movable components, in particular several movable segments, namely, an entire tabletop 4, and a head plate 14 and a leg plate 15 of the tabletop 4. The medical apparatus 1 further comprises a driven locking device 16 and a driven wheel 17.

The movable segments 4, 14, 15 are respectively driven by at least one driving device, such as an actuator, for example (not shown). The tabletop 4 is moved by a first driving device (not shown) in a vertical direction depicted by arrow H for adjusting a height of the tabletop 4. Further, the tabletop 4 is tilted by a second driving device (not shown) into a Trendelenburg position or an Anti-Trendelenburg position as depicted by arrow T. Furthermore, the tabletop 4 is displaced by a third driving device (not shown) along a longitudinal axis of the tabletop 4 as depicted by arrow L. The head plate 14 is tilted by a fourth driving device (not shown) as depicted by arrow TH and the leg plate 15 is tilted by a fifth driving device (not shown) as depicted by arrow TL. Alternatively, the medical apparatus 3 is provided with another number of driven movable segments 4, 14, 15, wherein at least one driven segment 4, 14, 15 movable in different directions is provided.

The driven locking device 16 comprises jack up stamps as support structures for securing a sure footing of the medical apparatus 1, i.e. for locking a motion of the entire operating table by touching a face supporting the operating table, i.e. a floor. The jack up stamps are lowered for touching the floor and, as the case may be, for lifting the operating table in order to lock the operating table. For moving the operating table, the jack up stamps are retracted and there is a gap between the jack up stamps and the face supporting the operating table. The jack up stamps are driven by a hydraulic drive. Alternatively, the jack up stamps are driven by electric drives or, further alternatively, the locking device is not provided, e.g., in case of a stationary operating table.

The driven wheel 17 is provided as a fifth wheel in a center of a chassis of the operating table additionally to wheels for moving the medical apparatus 1 in corners of the chassis of the operating table. The fifth wheel comprises a drive and the wheel moves the operating table by the drive when the wheel contacts the face supporting the operating table. Alternatively, also one or several of the wheels in the corners of the chassis of the operating table can be formed as the driven wheel 17 or, further alternatively, the driven wheel is not provided, e.g., in case of a stationary operating table.

The remote control 2 comprises a sensor 5. The sensor 5 comprises an inclinometer. Alternatively or additionally, the sensor 5 comprises another type of sensor, e.g., an acceleration sensors or a gyroscope combined with a geomagnetic sensor. The sensor 5 detects a position and a motion or an acceleration of the remote control 2.

Furthermore, the remote control 2 comprises seven release switches 6. The release switches 6 are respectively assigned to a specific motion of one of the driven movable segments 4, 14, 15, of the locking device 16, and of the driven wheel 17. By a first one of the release switches 6, the control of the vertical motion of the tabletop 4 can be released, by a second one of the release switches 6, the control of the tilting of the tabletop 4 into the Trendelenburg position or Anti-Trendelenburg position and a tilting around a longitudinal axis of the tabletop 4 can be released. A third one of the release switches 6 releases the control of the displacement of the tabletop 4 in the longitudinal direction of the tabletop 4, a fourth one of the release switches 6 releases the control of the tilting of the head plate 14, and a fifth one of the release switches 6 releases the control of the tilting of the leg plate 15. A sixth one of the release switches 6 releases the control of the locking device 16, i.e., initiates lifting or lowering the jack up stamps, and a seventh one of the release switches releases the control of the driven wheel 17 for driving the operating table. In a further alternative embodiment, another number of release switches 6, e.g., according to a number of motions of the movable components 4, 14, 15, 16, 17, merely one release switch 6, or more than two release switches 6, are provided.

The remote control 2 has an elongated shape and it has an axis A parallel to the elongated shape in an X axis direction of the remote control 2 and an axis B perpendicular to the elongated shape in a Y axis direction of the remote control 2. Alternatively, the remote control 2 does not have an elongated shape and the axes A and B, if necessary, are determined by definition. For reference, a third axis C, orthogonal to both axes A and B is also shown in the figures.

The remote control 2 further comprises a communication interface 7. The communication interface 7 establishes a communication 8 to the medical apparatus 3 in a wireless manner. Alternatively, the communication interface 7 has a connection cable and establishes the communication 8 to the medical apparatus 3 in a wired manner.

By the communication 8, the remote control 2 emits a control signal capable of controlling the motion of the movable components 4, 14, 15, 16, 17 according to a motion of the remote control 2 detected by the sensor 5 when the control of the motion of the driven movable components 4, 14, 15, 16, 17 is released by actuating the release switch 6. In particular, the remote control 2 emits the control signal according to a direction of the motion of the remote control 2 detected by the sensor 5 with respect to a position of the remote control 2 when the release switch 6 starts to release the motion. The remote control 2 emits the control signal according to an amount of the motion of the remote control 2. Additionally, the remote control 2 emits the control signal according to a speed of the motion of the remote control 2.

Alternatively, the amount and/or the speed of the motion of the remote control 2 are not considered, and, further alternatively, the direction of the motion is not considered but any motion is considered for moving the driven movable component 4, 14, 15, 16, 17, e.g., in a reciprocating manner.

By emitting the control signal, the remote control 2 is configured to control the direction of the motion of the driven movable components 4, 14, 15, 16, 17 according to the direction of the motion of the remote control 2 with respect to a position of the remote control 2 when the release button 6 starts to release the motion. Furthermore, the remote control 2 is configured to control a speed of the motion of the driven movable components 4, 14, 15, 16, 17 according to the amount of the motion of the remote control 2 with respect to the position of the remote control 2 when the release button 6 starts to release the motion, wherein the speed of the driven movable components 4, 14, 15, 16, 17 is the higher the larger the amount of the motion of the remote control 2 is. By reducing the amount of the motion of the remote control 2, the speed can be reduced. Optionally, a sensitivity of the remote control 2 can be adjusted. In case of a high sensitivity, 100% of the speed of the driven movable components 4, 14, 15, 16, 17 is achieved upon tilting of the remote control 2 of 30 degrees around one of the axes A or B. When a mid-sensitivity is set, 100% of the speed of the driven mobile components 4, 14, 15, 16, 17 is achieved upon tilting of the remote control 2 of 35 degrees around one of the axes A or B, and, when a low sensitivity is set, 100% of the speed of the driven mobile components 4, 14, 15, 16, 17 is achieved upon tilting of the remote control 2 of 45 degrees around one of the axes A or B. Alternatively, other appropriate values of the amount of tilting can be set.

Moreover, the remote control 2 is configured to control the speed of the motion of the driven movable components 4, 14, 15, 16, 17 according to the speed of the motion of the remote control 2, wherein the speed of the motion of the driven movable components 4, 14, 15, 16, 17 is the higher the higher the speed of the motion of the remote control 2 is. In alternative embodiments, the amount and/or the speed of the motion of the remote control 2 is not considered for the control of the speed of the driven movable components 4, 14, 15, 16, 17.

According to the manner of tilting the remote control 2, the speed of the motion can be adjusted between 1% and 100% of a nominal speed. Alternatively, an adjusted speed is fix independently from the manner of tilting the remote control 2.

The motion of the remote control 2 detected by the sensor 5 is a tilting around the axis B of the remote control 2 perpendicular to its elongated shape and a tilting around the longitudinal axis A of the remote control 2 parallel to its elongated shape. By the detection of the motion around the axis B of the remote control 2 perpendicular to its elongated shape, the vertical motion of the tabletop 4 and the displacement motions along the axis L are controlled. By tilting the remote control 2 in one direction, the tabletop 4 is lifted and, by tilting the remote control in the other direction, the tabletop 4 is lowered. By the detection of the motion around the axis A of the remote control 2 parallel to the elongated shape, the tilting motions of the table top 4, of the head plate 14, and of the leg plate 15 are controlled. In alternative embodiments, any of the motions are controlled either by detecting the motion around the axis A of the remote control 2, by detecting the motion around the axis B of the remote control 2, or by detecting the motion around the axis A and the axis B.

A combined motion of the remote control 2, i.e., the tilting around the axis B of the remote control 2 and the tilting around the longitudinal axis A of the remote control 2 controls several motions respectively driven by a driving device of one of the movable components 4, 14, 15, 16, 17. Upon an actuation of the release switch 6 assigned to the tabletop 4 and a tilting of the remote control 2 around the axis B, a control signal for approaching the Trendelenburg position or the Anti-Trendelenburg position is emitted and the motion is performed by the medical apparatus 1, and, simultaneously, when tilting the remote control 2 around the longitudinal axis A of the remote control 2, a control signal for tilting of the tabletop 4 according to a direction of the tilting of the remote control 2 is emitted and the motion is performed by the medical apparatus 1.

The leg section 15 is partitioned along the longitudinal axis of the tabletop 4 and it comprises a left leg section and a right leg section. Upward or downward motion of one of the left and right leg sections is actuated upon releasing the control of the leg section 15 by the respective release switch 6 and upon tilting the remote control 2 in a respective leftward or rightward direction and upward or downward for emitting a respective control signal by the remote control 2 and the motion is performed by the medical apparatus 1.

Figure 2:
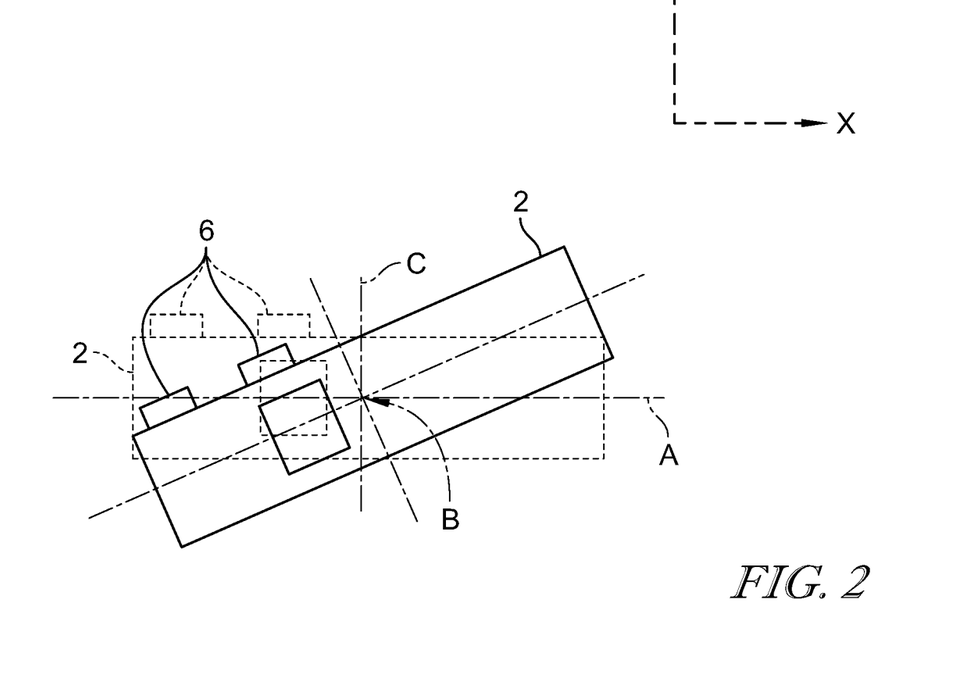
FIG. 2 shows a starting position and an end position of the remote control in a schematic side view when the remote control is tilted around an axis perpendicular to an elongated shape of the remote control for controlling a motion.

FIG. 2 shows a starting position and an end position of the remote control 2 in a side view when the remote control 2 is tilted around the axis B in the Y axis direction (FIG. 1) of the remote control 2 perpendicular to an elongated shape of the remote control 2 for controlling one of the motions. The initial position of the remote control 2 where the release switch 6 is actuated is depicted by dashed lines and the end position of the remote control 2 is depicted by solid lines. The speed and the direction of the motion of the driven movable components 4, 14, 15, 16, 17, the control of which is released by actuating the respective release switch 6, are determined by the movement of the remote control 2 around the axis B. In FIG. 2, in the initial position of the remote control 2, a Z axis of the remote control 2 is oriented vertically so the remote control 2 is oriented in a horizontal position.

Figure 3:
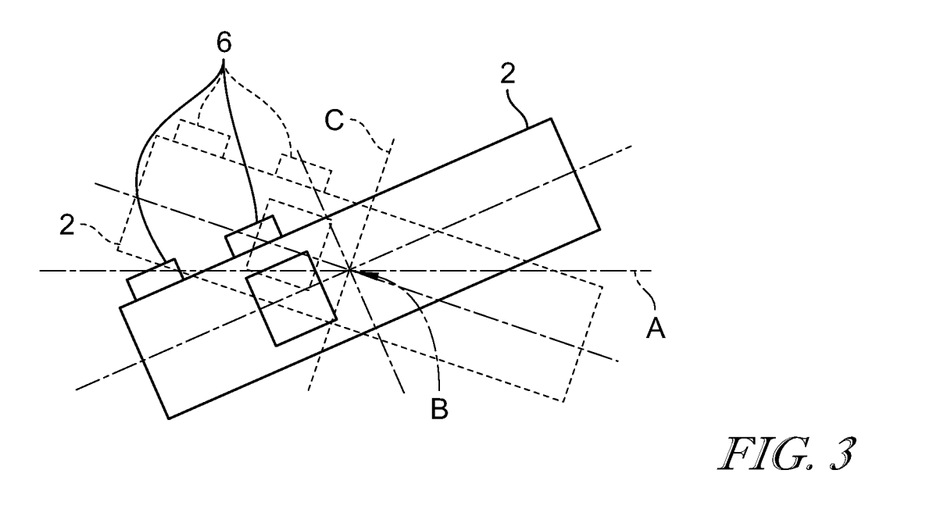
FIG. 3 shows another starting position and the end position of the remote control in the schematic side view when the remote control is tilted around the axis perpendicular to the elongated shape of the remote control for controlling a motion.

FIG. 3 shows another starting position and the end position of the remote control 2 of FIG. 2 in the side view when the remote control 2 is tilted around the axis B perpendicular to the elongated shape of the remote control 2 for controlling one of the motions. The initial position of the remote control 2 where the release switch 6 is actuated is depicted by dashed lines and the end position of the remote control 2 is depicted by solid lines. This figure shows that the motion of the driven components 4, 14, 15, 16, 17 of the medical apparatus 3 is not to be controlled compulsorily starting from the horizontal position of the remote control 2 but, also, another position is possible if the release switch 6 is actuated in this position and the remote control 2 is moved in a specific manner in order to control the motion.

Figure 4:
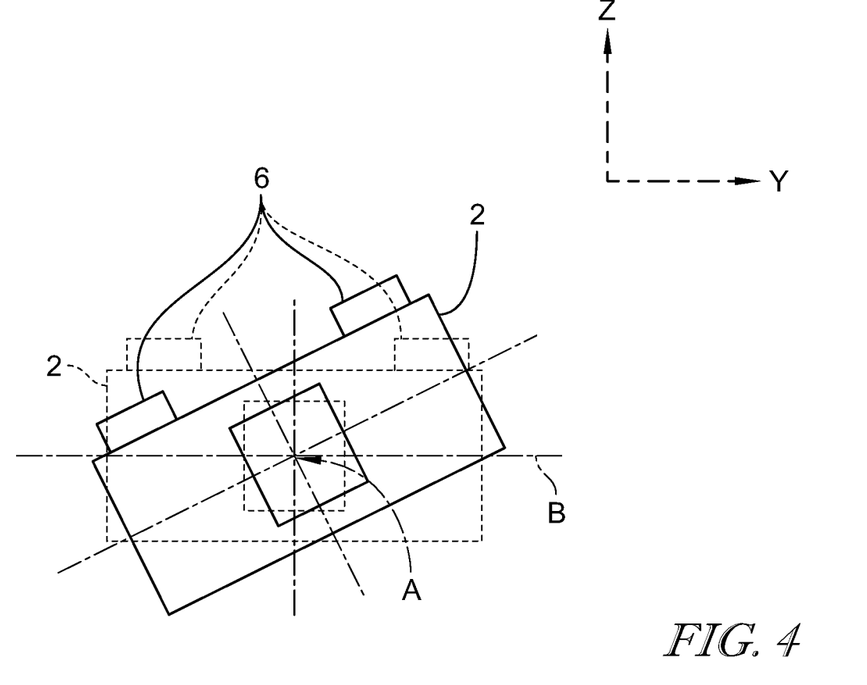
FIG. 4 shows a starting position and an end position of the remote control in a schematic front view when the remote control is tilted around an axis parallel to an elongated shape of the remote control for controlling a motion.

FIG. 4 shows the starting position and the end position of the remote control 2 in a front view when the remote control 2 is tilted around the axis A in the X axis direction (see FIG. 1) of the remote control 2 parallel to an elongated shape of the remote control 2. The initial position of the remote control 2 where the release switch 6 is actuated is depicted by dashed lines and the end position of the remote control 2 is depicted by solid lines. The speed and the direction of the motion of the driven movable components 4, 14, 15, 16, 17, the control of which is released by actuating the respective release switch 6, are determined by the movement of the remote control 2 around the axis A. In FIG. 4, in the initial position of the remote control 2, the Z axis of the remote control 2 is oriented vertically so the remote control 2 is oriented in a horizontal position.

Figure 5:
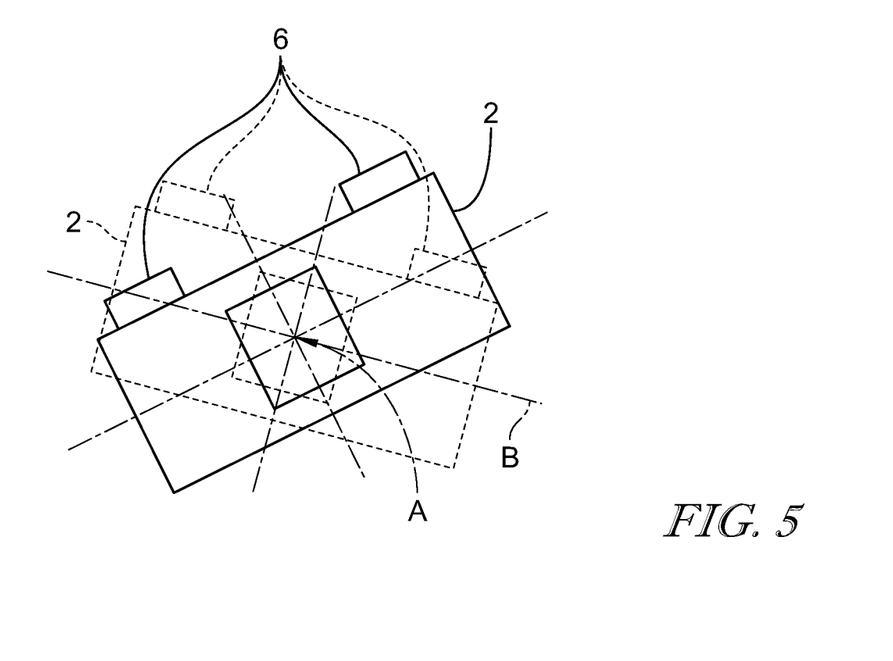
FIG. 5 shows another starting position and the end position of the remote control in the schematic front view when the remote control is tilted around the axis parallel to the elongated shape of the remote control for controlling a motion.

FIG. 5 shows another starting position and the end position of the remote control 2 of FIG. 4 in the front view when the remote control 2 is tilted around the axis A parallel to the elongated shape of the remote control 2 for controlling one of the motions. This figure shows that the motion of the driven components 4, 14, 15, 16, 17 of the medical apparatus 3 is not to be controlled compulsorily starting from the horizontal position of the remote control 2 but, also, another position is possible if the release switch 6 is actuated in this position and the remote control 2 is moved in a specific manner in order to control the motion.

Referring to FIGS. 2 to 5, the control signal according to the direction of the motion of the remote control 2 around at least one of the first axis A and the second axis B is only emitted if the motion of the remote control 2 around the at least one of the first axis A and the second axis B exceeds a predefined threshold. In this embodiment, the threshold is set to 3 degrees. In alternative embodiments, the threshold is set to other appropriate values, preferably between zero degrees and 6 degrees or no threshold is set.

Figure 6:
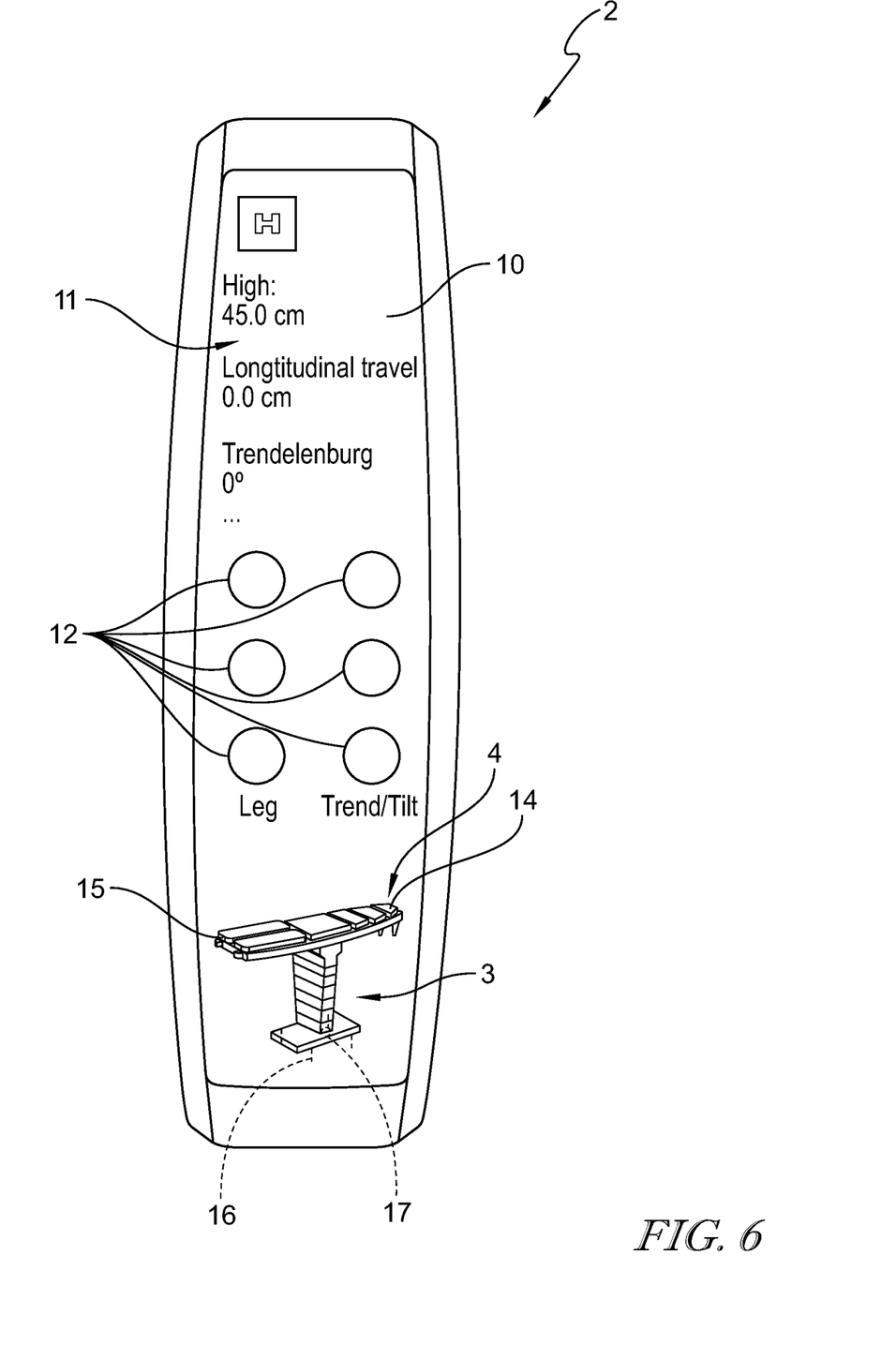
FIG. 6 shows a plan view of the remote control.

FIG. 6 shows a plan view of the remote control 2. The remote control 2 comprises a display 10 configured to detect a location of a touch of an object, wherein the display 10 is commonly denoted as a touchscreen. The object usually is a finger of an operator, i.e., of an operating room nurse.

The display 10 displays several operating states 11 of the operating table. These operating states are, e.g. a status as, e.g., a height, a longitudinal travel or a Trendelenburg angle, error messages, user information, etc. Further, the display 10 depicts soft keys 12 having an appearance of usual press buttons. Alternatively, the soft keys 12 have another appearance. When pressing one of the soft keys 12, one of the release switches 6 (not shown in FIG. 6) is actuated.

In a further area of the display 10, an illustration of the medical apparatus 3 is depicted. The display 10 is further configured to display a preview of the motion of the at least one driven movable component 4, 14, 15, '", 17 according to the control signal so as to depict a live preview of the motions.

Figure 7:
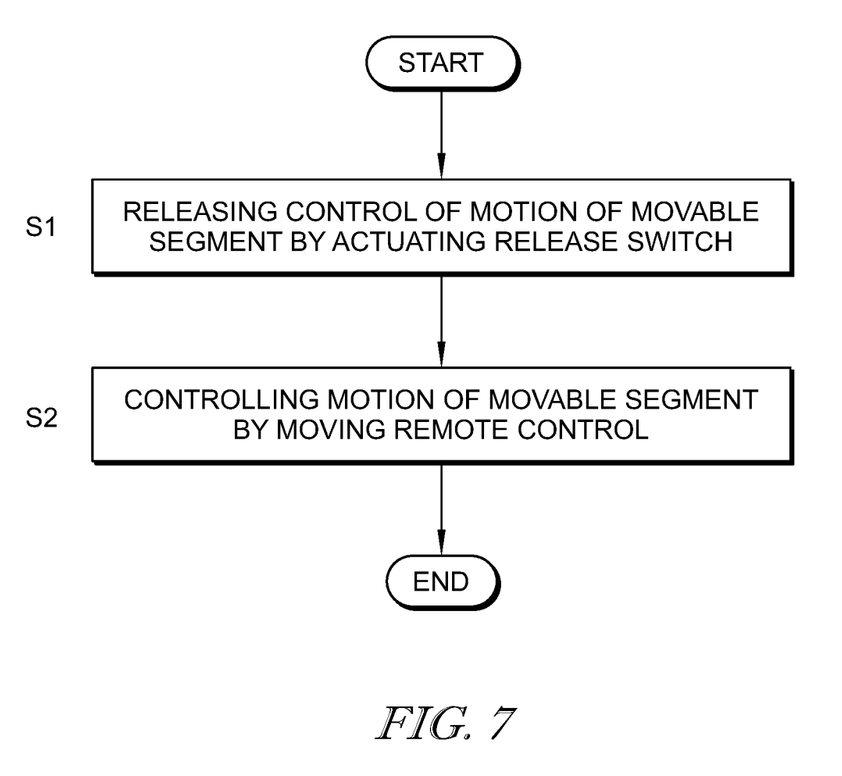
FIG. 7 shows a flow chart of a method according to the present disclosure.

FIG. 7 shows a flow chart of a method according to the present disclosure.

In use, in a first step S1, the control of a specific one of the motions of the driven movable components 4, 14, 15, 16, 17 of the medical apparatus 3 is released by actuating a specific release switch 6 of the remote control 2 assigned to the specific motion.

In a next step S2, the motion of the specific one of the movable components 4, 14, 15, 16, 17 is controlled by moving the remote control 2 with respect to a position of the remote control 2 when the specific release switch 6 is actuated.

The direction of the motion of the specific one of the driven movable components 4, 14, 15, 16, 17 is defined by the direction of motion of the remote control 2 around the axis B perpendicular to an elongated shape of the remote control 2 and/or around the axis A parallel to the elongated shape of the remote control 2.

The remote control 2 emits a stop command for stopping the motion of the driven movable components 4, 14, 15, 16, 17 when the remote control 2 is moved into a horizontal position so that the motion of the specific one of the driven movable components 4, 14, 15, 16, 17 is stopped. This function is not compulsorily and, alternatively, the motion is stopped when the release switch 6 is not actuated anymore and the release switch 6 does not release the command anymore. The horizontal position is detected by the inclinometer or, alternatively, by the acceleration sensor. The acceleration sensor detects components of acceleration forces in the directions of three axes X, Y, Z of the remote control 2. If the component of the acceleration force in the direction of the Z axis of the remote control 2 amounts 1 g, the remote control 2 is determined as being oriented in the horizontal position.

Although this disclosure refers to specific embodiments, it will be understood by those skilled in the art that various changes in form and detail may be made without departing from the subject matter set forth in the accompanying claims. Other variations to the disclosed embodiments can be understood and effected by those skilled in the art in practicing the claimed invention, from a study of the drawings, the disclosure and the appended claims. Such modifications may involve other features, which are already known in the art and may be used instead of or in addition to features already described herein. In the claims, the word "comprising" does not exclude other elements or steps, and the indefinite article "a" or "an" does not exclude a plurality.

The invention claimed is:

1. A remote control for controlling a medical apparatus having a plurality of driven movable components, the remote control comprising:
    a sensor configured to detect a position and a motion of the remote control, and
    a plurality of release switches, each release switch corresponding to a specific driven movable component,
    wherein the remote control emits a control signal controlling a motion of a specific driven movable component according to a motion of the remote control detected by the sensor when a control of the motion of the specific driven movable component is released by actuating the specific release switch corresponding to the specific driven movable component is released, the specific release switch operational to release only the specific driven movable component to thereby prevent the motion of the remote control detected by the sensor from being inadvertently interpreted as corresponding to a driven movable component other than the specific driven movable component corresponding to the specific release switch,
    wherein one of the at least one driven movable components is formed by a wheel of the medical apparatus, wherein the wheel contacts a floor supporting the medical apparatus and comprises a drive and the wheel is configured to move the medical apparatus over the floor by the drive under the control of the remote control,
    wherein the remote control has an elongated shape and a first axis (A) parallel to the elongated shape of the remote control and a second axis (B) perpendicular to the elongated shape of the remote control, and
    wherein the remote control is configured to emit the control signal according to a direction of the motion of the remote control around at least one of the first axis (A) and the second axis (B).

2. The remote control of claim 1, wherein the remote control is configured to emit the control signal according to a direction of the motion of the remote control detected by the sensor with respect to a position of the remote control when the at least one release switch is actuated to start the release of the control of the motion of the at least one driven movable component.

3. The remote control of claim 1, wherein the remote control is configured to emit the control signal according to an amount of the motion of the remote control.

4. The remote control of claim 1, wherein the remote control is configured to emit the control signal according to a speed of the motion of the remote control.

5. The remote control of claim 1, wherein the remote control comprises a display configured to detect a location of a touch of an object.

6. The remote control of claim 1, wherein the remote control comprises a display configured to display a preview of a motion of the at least one driven movable component according to the control signal.

7. The remote control of claim 1, wherein the remote control is configured to control a direction of the motion of a driven movable component according to a direction of the motion of the remote control with respect to a position of the remote control when the at least one release switch starts to release the control of the motion.

8. The remote control of claim 1, wherein the remote control is configured to emit the control signal according to the direction of the motion of the remote control around at least one of the first axis (A) and the second axis (B) if the motion of the remote control around the at least one of the first axis (A) and the second axis (B) exceeds a predefined threshold.

9. The remote control of claim 8, wherein the remote control is configured to control a direction of the motion of a driven movable component according to a direction of the motion of the remote control with respect to a position of the remote control when the specific release switch starts to release the control of the motion.

10. The remote control of claim 8, wherein the remote control comprises several release switches,
the medical apparatus comprises several movable components respectively driven by a driving device, and
the several release switches are respectively assigned to a specific motion of one of the driven movable components.

11. The remote control of claim 8, wherein
the medical apparatus comprises at least one driven movable component which performs several motions respectively driven by a driving device, and
the system is configured such that the several motions are controlled by the remote control when the several motions of the at least one driven movable component are released by a release button assigned to the at least one driven movable component, wherein the several motions are controlled according to the motions of the remote control around a first axis (A) parallel to an elongated shape of the remote control and a second axis (B) perpendicular to the elongated shape of the remote control.

12. The remote control of claim 8, wherein one of the at least one driven movable components is formed by a locking device configured to lock a motion of the operating table by touching a face supporting the operating table.

13. The remote control of claim 1, wherein the remote control is configured to control a direction of the motion of the at least one driven movable component according to a direction of the motion of the remote control with respect to a position of the remote control when the at least one release switch starts to release the control of the motion.

14. The remote control of claim 1, wherein
the medical apparatus comprises at least one driven movable component which performs several motions respectively driven by a driving device, and
the system is configured such that the several motions are controlled by the remote control when the several motions of the at least one driven movable component are released by a release button assigned to the at least one driven movable component, wherein the several motions are controlled according to motions of the remote control around the first axis (A) parallel to an elongated shape of the remote control and the second axis (B) perpendicular to the elongated shape of the remote control.

15. The remote control of claim 1, wherein one of the at least one driven movable components is formed by a locking device configured to lock a motion of the medical apparatus by touching a face supporting the medical apparatus.

16. A method for operating a medical apparatus by means of a remote control with the steps:
releasing a control of a motion of a specific one of a plurality of driven movable components of the medical apparatus by actuating a specific release switch of the remote control corresponding to a specific driven movable component, the specific release switch operational to release only the specific driven movable component to thereby prevent the motion of the remote control from being inadvertently interpreted as corresponding to a driven movable component other than the specific driven movable component corresponding to the specific release switch, and
controlling a motion of the specific driven movable component by moving the remote control with respect to a position of the remote control when the specific release switch starts to release the control of the motion of the specific driven movable component,
wherein at least one of the specific one of the driven movable components includes a wheel that contacts a floor supporting the medical apparatus and comprises a drive and the wheel is configured to move the medical apparatus over the floor by the drive.

17. The method of claim 16, wherein a direction of the motion of the specific one of the driven movable components is defined by a direction of motion of the remote control around at least one of an axis (A) parallel to an elongated shape of the remote control and an axis (B) perpendicular to the elongated shape of the remote control.

18. The method of claim 17, wherein the motion of the specific one of the driven movable components is stopped when the remote control is moved into a horizontal position.

19. The method of claim 16, wherein at least one of the specific one of driven movable components includes a jack that moves into engagement with the floor to prevent movement of the medical apparatus over the floor.

20. The remote control of claim 1, wherein at least one of the specific one of driven movable components includes a jack that moves into engagement with the floor to prevent movement of the medical apparatus over the floor.

* * * * *